United States Patent
Christiansen et al.

(10) Patent No.: US 10,779,749 B2
(45) Date of Patent: Sep. 22, 2020

(54) DISPOSABLE ADHESIVE SUBSTRATE ADAPTED TO BE ARRANGED ON A MEDICAL DEVICE

(71) Applicant: Sunstar Suisse SA, Etoy (CH)

(72) Inventors: Christian Christiansen, Birkerod (DK); Morten Haugland, Svenstrup J (DK); Tommy Jacobsen, København Ø (DK); Karsten Videbæk, Jyllinge (DK)

(73) Assignee: Sunstar Suisse SA, Etoy (CH)

( * ) Notice: Subject to any disclaimer, the term of this patent is extended or adjusted under 35 U.S.C. 154(b) by 304 days.

(21) Appl. No.: 15/740,515

(22) PCT Filed: Jun. 29, 2016

(86) PCT No.: PCT/EP2016/065133
§ 371 (c)(1),
(2) Date: Dec. 28, 2017

(87) PCT Pub. No.: WO2007/001470
PCT Pub. Date: Jan. 5, 2017

(65) Prior Publication Data
US 2018/0184939 A1   Jul. 5, 2018

(30) Foreign Application Priority Data
Jun. 30, 2015 (EP) ..................... 15174601

(51) Int. Cl.
*A61B 5/0492* (2006.01)
*A61B 5/00* (2006.01)
(Continued)

(52) U.S. Cl.
CPC .......... *A61B 5/0492* (2013.01); *A61B 5/4557* (2013.01); *A61B 5/6833* (2013.01); *A61B 2560/0214* (2013.01); *A61B 2560/0456* (2013.01); *A61B 2562/04* (2013.01); *A61B 2562/043* (2013.01); *A61B 2562/164* (2013.01); *A61N 1/0452* (2013.01); *A61N 1/0492* (2013.01); *A61N 1/36014* (2013.01); *H02J 7/025* (2013.01); *H02J 50/10* (2016.02)

(58) Field of Classification Search
CPC ............ A61B 5/04085; A61B 5/04087; A61B 5/0416; A61B 5/0492
USPC ................................... 600/391–393
See application file for complete search history.

(56) References Cited

U.S. PATENT DOCUMENTS 6,385,473 B1 * 5/2002 Haines ................. A61B 5/0006
600/382
8,214,007 B2 * 7/2012 Baker .................. A61B 5/0006
600/372
(Continued)

FOREIGN PATENT DOCUMENTS

CN   201073301 Y   6/2008
CN   201929957 U   8/2011
(Continued)

*Primary Examiner* — Lee S Cohen
(74) *Attorney, Agent, or Firm* — Dinsmore & Shohl LLP (57) ABSTRACT

A disposable adhesive substrate, a medical device and a charging station are provided. In particular the substrate may be adapted to be arranged on the medical device, which correspondingly may be charged in the charging station. The medical device may be used for monitoring and treatment of bruxism.

15 Claims, 7 Drawing Sheets

(51) Int. Cl.
    *A61N 1/36*     (2006.01)
    *A61N 1/04*     (2006.01)
    *H02J 50/10*     (2016.01)
    *H02J 7/02*     (2016.01)

(56) References Cited

U.S. PATENT DOCUMENTS

| | | |
|---|---|---|
| 9,510,762 B2 * | 12/2016 | Datovech ........... A61B 5/04085 |
| 2010/0222734 A1 | 9/2010 | Jayes et al. |
| 2013/0325096 A1 | 12/2013 | Dupelle et al. |
| 2015/0174392 A1 | 6/2015 | Stringdahl et al. |

FOREIGN PATENT DOCUMENTS

| | | |
|---|---|---|
| EP | 1275342 A2 | 1/2003 |
| KR | 20140004168 U | 7/2014 |
| KR | 20140088390 A | 7/2014 |
| RU | 2530562 C2 | 10/2014 |
| WO | 2013121415 A1 | 8/2013 |
| WO | 2015036420 A1 | 3/2015 |

\* cited by examiner

DISPOSABLE ADHESIVE SUBSTRATE ADAPTED TO BE ARRANGED ON A MEDICAL DEVICE

CROSS-REFERENCE TO RELATED APPLICATIONS

This application is the U.S. national stage of PCT/EP2016/065133 filed Jun. 29, 2016, which claims priority of European Patent Application 15174601.3 filed Jun. 30, 2015 of which is hereby incorporated by reference in its entirety.

The present disclosure relates to a disposable adhesive substrate, a medical device and a charging station. In particular the substrate may be adapted to be arranged on the medical device, which correspondingly may be charged in the charging station, with or without the substrate. The medical device may be used for monitoring and treatment of bruxism.

BACKGROUND

Medical devices for monitoring or applying electric energy to the body are generally known in the art. For instance, muscles can be monitored, e.g. for diagnostic purposes, by measuring the electric signals involved in muscle contraction or they can be stimulated, e.g. for therapeutic purposes, by applying electrical signals to the skin. This monitoring and stimulation can be provided by means of electrodes and in order to ensure contact with the skin the electrodes can be provided with an adhesive and conductive material. Electrically conductive adhesive solid hydrogels and liquid gels can provide this electrical interface to the skin. The conductive material can be applied to the electrode at the electrode manufacturer such that the material cannot be removed from the electrode and reused. However, once the electrode with conductive material has been in contact with a patient, it is generally not desirable to apply the same electrode with the same conductive material to a different patient. Thus, for the electrodes to be reusable the electrodes and the conductive material must be configured such that the conductive material can be applied and removed and new conductive material re-applied when needed. This operation is typically purely manual and with medical devices for home use, it may even be the patient that applies the conductive material. To assist the user in applying the conductive material can be made part of a disposable adhesive substrate (aka "gel-pad") that is applied to the medical device by the user shortly before use. In order for the medical device to function optimally it may be of utmost importance that the adhesive substrate is placed at exactly the correct position, e.g. in relation to electrodes, for the medical device to function optimally.

SUMMARY OF THE PRESENT DISCLOSURE

The circumferential outline, i.e. outside shape, of the adhesive substrate and the arrangement of the conductive material should be formed such that the substrate is easy to apply to the medical device and such that conductive material matches the configuration of the electrodes. The present disclosure in a first aspect relates to a disposable adhesive substrate, preferably adapted to be arranged on a medical device having electrodes, such as EMG electrodes. The substrate preferably comprises at least a first adhesive, e.g. a first adhesive layer, on a first side of the substrate, e.g. configured for attaching the substrate to the medical device. The substrate may further comprise at least a second adhesive, e.g. a second adhesive layer, on a second opposite side of the substrate, preferably configured for attaching the substrate to the skin of a user of the medical device. The substrate may further comprise conductive contact areas, which may be configured for providing electrical connection between the electrodes and e.g. the skin of a user of the medical device. The circumferential outline of the substrate may be rotationally asymmetric around any two perpendicular rotation axes in the plane of the substrate.

The inventor has however realized that even though prior art substrates are matched to a specific electrode configuration on a medical device and provided with guidance to the user on how to apply the substrate, the users in many instances apply the substrates in the wrong way, especially in the case where the substrate is a double adhesive, i.e. with adhesives on both sides of the substrate, whereas the conductive material is typically provided on only one (adhesive) side of the substrate, which side must be in contact with the skin of the user. This can result in the conductive material not being arranged in the correct configuration in order to ensure electrical connection between skin and electrodes. The problem is that at least initially the medical device might function properly because even if arranged improperly the substrate might establish a (poor) electrical connection between skin and electrodes that might "fool" the medical device and consequently the user to believe that the substrate is arranged properly. The solution is to make sure that the substrate has a shape and/or a configuration that ensures a one-to-one correspondence with a specific medical device. I.e. the substrate must be configured such that it can only be mounted in one unique way on the medical device. One solution is that the substrate is asymmetric, e.g. that the circumferential outline of the substrate is asymmetric, e.g. asymmetric along an axis through (the middle/centre of) the substrate and/or asymmetric along two axes, e.g. perpendicular axes, through (the middle/centre of) the substrate. In one embodiment the presently disclosed substrate is asymmetric around any rotation axis, e.g. any rotation axis in the plane of the substrate and/or a rotation axis which is perpendicular to the plane of the substrate. Hence, the circumferential outline of the substrate may be configured to be laterally irreversible in the plane of the substrate. Asymmetry may also be provided from the location of the conductive contact areas on the substrate because the arrangement of the conductive contact areas typically is adapted to match the location of the electrodes.

Even though the substrate is asymmetric it may also be advantageous if the circumferential outline of the substrate is configured to match a shape of the medical device, i.e. the shape of an electrode assembly, a slot, groove, trace, recess, etc. of the medical device whereon or wherein the substrate can be attached in only one configuration where the conductive material of the conductive contact areas are facing the skin of the user of the medical device in the correct configuration.

Another aspect of the present disclosure relates to a medical device for monitoring muscular activity of an individual comprising a housing for accommodating a power source, a control unit and a processing unit, two wings bendably attached to opposite sides of the housing, and at least three electrodes, such as EMG electrodes, mounted and distributed on the housing and each wing such that the electrodes extend substantially in a plane across the housing and the wings. E.g. a reference electrode in the middle and two outer signal electrodes. The medical device may be configured such that the wings can flexibly and/or elastically adapt to 1) the local contour of the skin of the individual, 2) to movement of the individual, and/or to muscular flexion and/or abduction of the individual. The medical device is preferably configured to receive a disposable adhesive substrate in the electrode plane on the surface of the housing, a substrate such as the disposable adhesive substrate as herein disclosed.

Yet another aspect of the present disclosure relates to a charging station for a wireless battery driven medical device comprising a housing with an upper cover, the upper cover having a recess shaped to hold the medical device in a one-to-one correspondence. The contour of the recess may be at least partly rounded such that the recess is configured to match a rounded medical device, e.g. the medical device as herein disclosed.

A further aspect relates to a kit of parts comprising the medical device and the charging station as herein disclosed, wherein the medical device and the charging station are configured such that the medical device matches the recess of the charging station.

DESCRIPTION OF DRAWINGS

FIG. 1b is a front view of the substrate of FIG. 1a.

FIG. 1c shows a perspective illustration of the substrate of FIG. 1a.

FIG. 2b shows a perspective top view of the medical device of FIG. 2a.

FIG. 2c shows a top view of the medical device of FIG. 2a.

FIG. 3b is a cut-through perspective illustration of the substrate and foil of FIG. 3a.

FIG. 13a shows a perspective illustration of the recess and a circuit board of the charging station of FIG. 7a.

DETAILED DESCRIPTION OF THE INVENTION

Substrate

As stated above a first aspect of the present disclosure relates to a disposable adhesive substrate. In one embodiment the substrate is adapted to be arranged on a medical device having EMG electrodes, the substrate comprising a first adhesive layer on a first plane side of the substrate configured for attaching the substrate to the medical device, a second adhesive layer on a second opposite plane side of the substrate configured for attaching the substrate to the skin of a user of the medical device, and conductive contact areas configured for providing electrical connection between the EMG electrodes and the skin of a user of the medical device, Wherein the circumferential outline of the substrate is rotationally asymmetric around any two perpendicular rotation axes in the plane of the substrate. In one embodiment the circumferential outline of the substrate is asymmetric around every perpendicular rotation axis in the plane of the substrate. The substrate may be elongated, e.g. along the direction of extension of the conductive contact areas. A prior art substrate for a medical device is disclosed in WO 2014/001520.

The substrate is preferably configured to form an adhesive bond between a medical device, such as herein disclosed, and the skin of a user of the medical device. The substrate is preferably further configured to form a conductive connection between the EMG electrodes and the skin of the user. The substrate is preferably flexible and/or bendable. The thickness of the substrate may be less than 2 mm, more preferably less than 1 mm, however in a limited area around the electrode contact areas the conductive material may increase the height of the substrate to around 2 mm, i.e. a maximal thickness of the substrate of less than 3 mm, more preferably less than 2.5 mm, most preferably less than 2.2 mm.

One embodiment of the presently disclosed substrate is shown in FIGS. 1a-c, FIG. 3a-b, FIG. 4 and FIG. 6. The substrate 1 is substantially plane and comprises three conductive contact areas 4 with a first adhesive surface 2 configured for attaching the substrate to a medical device and a second adhesive surface 3 (opposite the first adhesive surface 2) configured for adhesive contact with skin such that adhesive and conductive contact is established between the medical device and the skin of a user of the medical device. In the illustrated embodiment the conductive contact areas 4 of the substrate 1 are not arranged in a line, which can be seen in FIG. 1b—the conductive contact areas 4 are actually arranged such that the centres of the conductive contact areas 4 follow an arc of a circle and are also forming an isosceles triangle. The circumferential outline of the substrate 1 also substantially follows the bend of the conductive contact area which is visualized in FIG. 6. The circumferential outline of the substrate 1 further comprises two cut-outs 5, 5' which are also visualized in FIG. 6.

Figure 1A:
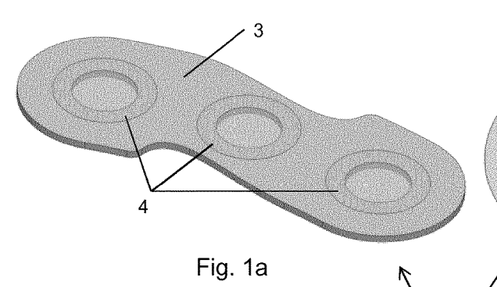
FIG. 1a shows a perspective drawing of one embodiment of the presently disclosed asymmetric disposable adhesive substrate.
Figure 1B:
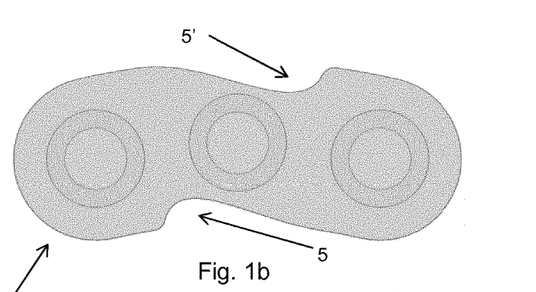
Figure 1C:
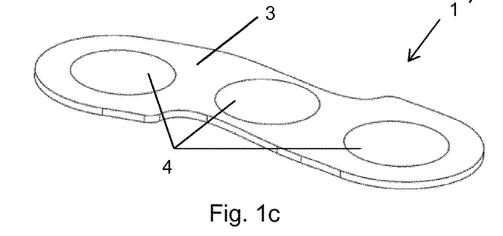
Figure 4:
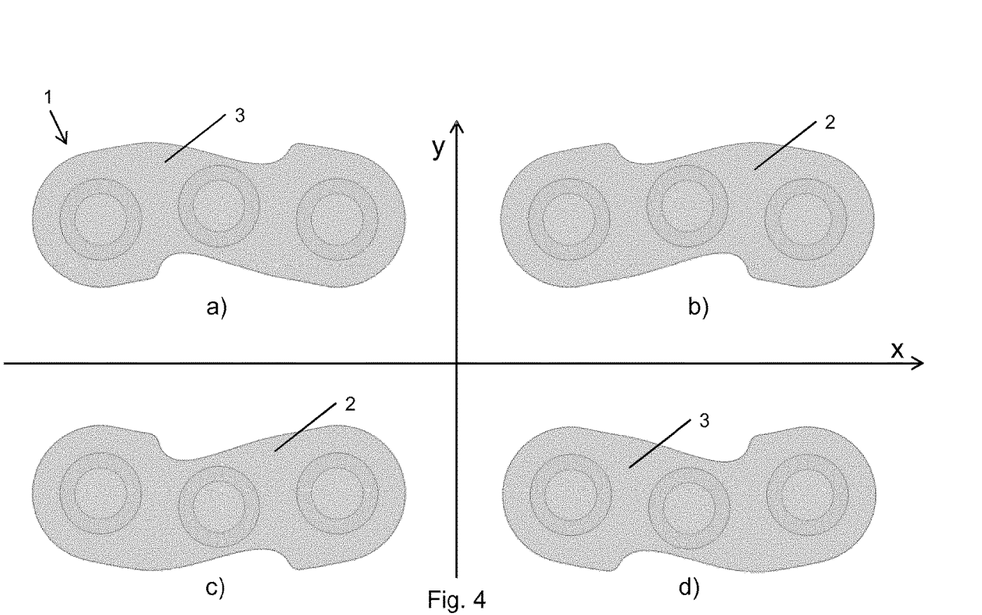
FIG. 4 shows the substrate of FIG. 1 when reflected in/rotated around two perpendicular axes in the plane of the substrate.

The design of the substrate exemplified in FIG. 1 is further visualized in FIG. 4. FIG. 4a corresponds to FIG. 1b. FIG. 4b shows the substrate of FIG. 4a which has been reflected in the (vertical) Y-axis shown in FIG. 4. Such a reflection corresponds to a 180° rotation around an axis in the plane of the substrate 1 through the centre of the substrate 1 and parallel with the Y-axis. FIG. 4c shows the substrate of FIG. 4a which has been reflected in the (horizontal) X-axis shown in FIG. 4. Such a reflection corresponds to a 180° rotation around an axis in the plane of the substrate 1 through the centre of the substrate 1 and parallel with the X-axis. Finally FIG. 4d shows the substrate of FIG. 4b reflected in the X-axis which also corresponds to the substrate of FIG. 4c reflected in the Y-axis. FIG. 4d is also the result of a rotation of 180° of the substrate in FIG. 4a around an axis perpendicular to the plane of the substrate.

Figure 5:
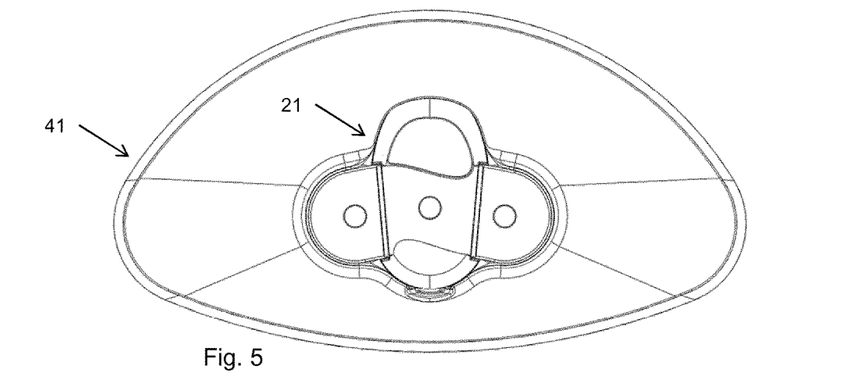
FIG. 5 shows the bottom of the medical device of FIG. 2 when located in one embodiment of the presently disclosed charging station.
Figure 6:
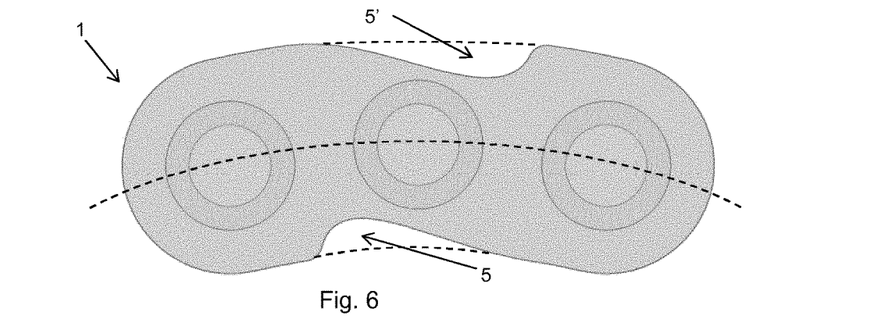
FIG. 6 shows the substrate of FIG. 1 where the two cut-outs in the circumferential outline of the substrate have been highlighted.

FIG. 5 shows the bottom of one embodiment of the presently disclosed medical device 21 when located in one embodiment of the presently disclosed charging station 41. The medical device 21 is also illustrated in FIG. 2. The medical device 21 comprises three electrodes 23, 23', 30 and protrusions 25, 25' and is configured to receive a disposable adhesive substrate on top of the electrodes and between the protrusions. The substrate 1 of FIG. 4 is configured to match the medical device 21. FIG. 4 shows the four most likely orientations of the substrate 1 a user of the medical device 21 would choose between when facing the task of applying the substrate 1 to the medical device 21 because the conductive contact areas 4 in FIGS. 4a-d are arranged along the longitudinal extension of the electrodes 23, 23', 30 of the medical device 21. When comparing FIG. 4 and FIG. 5 it is clear that only when the substrate 1 is arranged as illustrated in FIG. 1 it will match the medical device 21 in FIG. 5:

Regarding FIG. 4c the bend and the cut-outs 5, 5' of the substrate 1 and arrangement of the conductive contact areas 4 ensure that the orientation of the substrate illustrated in FIG. 4c cannot be attached to the medical device 21.

Regarding FIG. 4d the bend the substrate 1 and arrangement of the conductive contact areas 4 ensure that the orientation of the substrate illustrated in FIG. 4d cannot be attached to the medical device 21.

Regarding FIG. 4b the cut-outs 5, 5' of the substrate 1 ensures that the orientation of the substrate illustrated in FIG. 4b cannot be attached to the medical device 21.

Hence, with the orientation of FIG. 4b it is only the cut-outs 5, 5' that prevents the substrate 1 to be attached to the medical device—if a user tries this FIG. 4b configuration of the substrate 1 on the medical device 21 the protrusions 25, 25' makes it impossible to attach the substrate to the medical device. The drawings are only exemplary but illustrate that a disposable adhesive substrate can be provided with an asymmetric circumferential outline that helps a user with applying the substrate in the correct orientation and configuration on a medical device to ensure correct operation of the medical device.

In one embodiment the substrate comprises at least three of said conductive contact areas wherein the circumferential outline is axially asymmetric along an axis perpendicular to a line connecting the centres of the outermost contact areas.

In a further embodiment the substrate comprises at least three of said conductive contact areas arranged in fixed isosceles triangular relationship one to another, wherein the circumferential outline of the substrate is axially asymmetric along an axis through the centre of the middle contact area which is perpendicular to a line connecting the centres of the outermost contact areas.

In yet a further embodiment the substrate the circumferential outline of the substrate is axially asymmetric along a long axis in the plane of the substrate and axially asymmetric along an axis perpendicular to the long axis in the plane of the substrate.

The substrate may be configured to match one or more slot(s) and/or groove(s) on the medical device, preferably such that the substrate and the medical device have a one-to-one attachment correspondence. One way of providing a correspondence with a slot/groove is to provide one, two or more cut-outs in the circumferential outline of the substrate. Each cut-out may for example be shaped like an asymmetric wave pulse as exemplified in FIG. 6. Each cut-out may be rounded as also exemplified in the drawings. Further, the cut-outs may be asymmetrically arranged along the circumferential outline of the substrate. One possible result is that the circumferential outline of the substrate may be substantially S-shaped as seen in the drawings. Hence, the shape of the cut-outs may be configured to match a slot/groove on the medical device, such that the substrate and the medical device has a one-to-one attachment correspondence. An exemplified shape of the cut-outs 5, 5' are visualized in FIG. 6 where stippled lines indicate the circumferential outline of the substrate 1 without the cut-outs 5, 5'.

In a further embodiment the substrate comprises apertures. Preferably each of said contact areas at least partly encircles a corresponding aperture and the location and size of said apertures are preferably configured to match the location and size of the EMG electrodes of the medical device. The presently disclosed substrate may comprise at least three of such apertures arranged in a fixed spatial relationship one to another, such as arranged in a fixed triangular relationship one to another. The at least three apertures may be arranged such that the centres of said apertures are not on a line. Possibly the at least three apertures may be arranged such that the centres of said apertures lie on a line which is an arc of a circle having a radius of from 60-200 mm. In another embodiment he centres of the apertures are arranged in a triangular arrangement in which the longest side of the triangle so defined is not more than 40 mm. Such arrangements of the apertures are exemplified and visualized in FIG. 6 where a stippled line indicated the bending of the substrate 1 and the arrangement of the apertures.

Figure 3A:
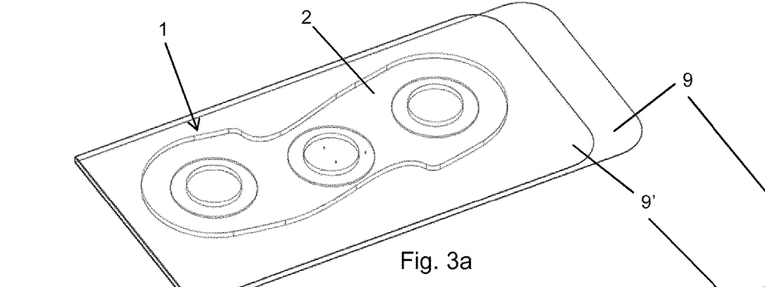
FIG. 3a shows a perspective illustration of the substrate of FIG. 1 sandwiched between two protective foils.
Figure 3B:
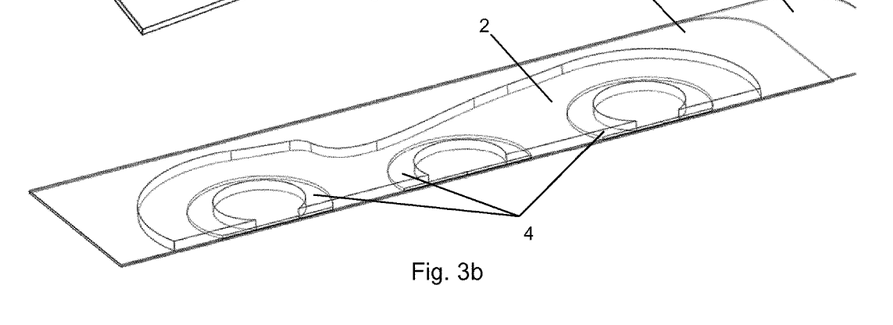

The presently disclosed substrate may further comprise two layers of removable protective sheet located on each plane side of the substrate as illustrated in FIG. 3a-b, i.e. the substrate 1 is sandwiched between these protective sheets 9, 9'. The substrate 1 is stored with these sheets 9, 9' to protect and maintain the adhesiveness of the adhesive layers 2, 3. The protective sheets 9, 9' are preferably configured to be removed before use of the substrate 1 and may be arranged such that one sheet 9' is initially removed from the substrate exposing the adhesive side 2 of the substrate 1 that is attached to the medical device 21. After attachment to the medical device 21 the other protective sheet 9 can be removed from the substrate 1.

FIG. 3 also illustrates a possible configuration of the conductive contact areas 4 which is best visualized in the cut-through illustration in FIG. 3b showing the three conductive contact areas 4 encircling three apertures but are only exposed on the side 3 of the substrate 1 that is supposed to be attached to the skin of the user whereas the conductive contact areas 4 do not extend through the full thickness of the substrate 1.

Medical Device

As previously stated another aspect of the present disclosure relates to a medical device for monitoring muscular activity of an individual comprising a housing for accommodating a power source, a control unit and a processing unit, two wings bendably attached to opposite sides of the housing, and at least three electrodes, such as EMG electrodes, mounted and distributed on the housing and each wing such that the electrodes extend substantially in a plane across the housing and the wings. Exemplary medical devices and EMG electrode assemblies, e.g. for monitoring and treatment of bruxism, are disclosed in PCT application WO 2004/087258, WO 2009/036769, WO 2009/036770 and WO 2010/099796. These documents are hereby incorporated by reference in their entirety.

An exemplary embodiment of the presently disclosed medical device is shown in the drawings, in particular FIGS. 2, 5 and 7-13, where the medical device substantially looks like a bumblebee. With the presently disclosed medical device a wireless all-in-one bruxism monitoring and treatment device for home/private use can be realized, a device that is both easy to use and comfortable to wear, also during night. As stated above the medical device is preferably configured such that the wings can flexibly and/or elastically adapt to 1) the local contour of the skin of the individual, 2) to movement of the individual, and/or to muscular flexion and/or abduction of the individual. The flexibility of the wings helps to provide a better contact with the muscles of the temple region, where the contour can be both concave and convex. The flexibility of the wings further helps to maintain the contact with the user during e.g. muscle contraction and in general when the user is moving.

Hence, the presently disclosed medical device may be configured such that the two wings are elastically bendable in the plane of the electrodes. The two wings may be hingedly attached to the housing as exemplary illustrated in FIG. 12, where the upper electrode side of each wing is bendably attached to the upper side of the housing by means of a thinned connection formed by an elongated groove in the shell of the housing. Accordingly the connection between the lower side of each wing (opposite the electrodes) and the housing may be formed by means of an edge of the wing which is adapted to slide on a corresponding edge of the housing.

Figure 12A:
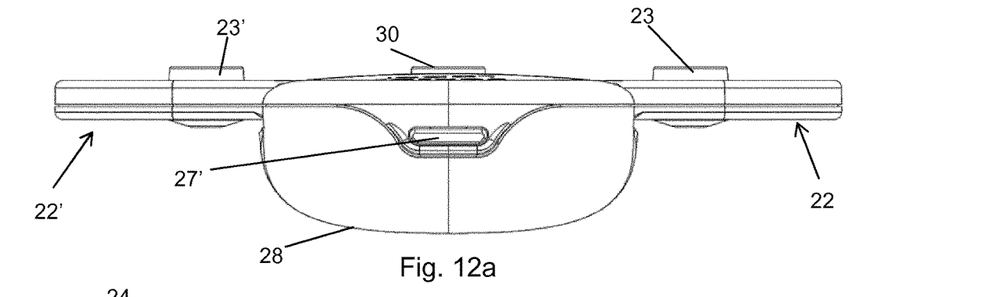
FIG. 12a is a view from the back of the medical device of FIG. 2.
Figure 12B:
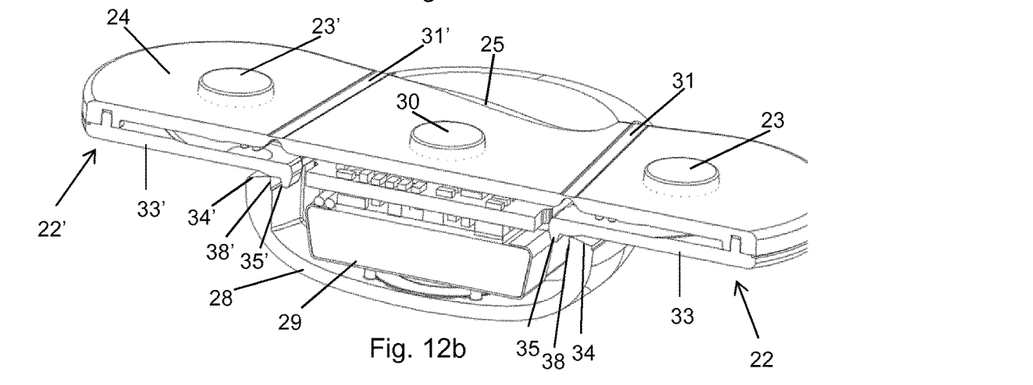
FIG. 12b shows a cut-through perspective illustration of the medical device of FIG. 2 at least partly illustrating the hinged attachment of the flexible wings.
Figure 12C:
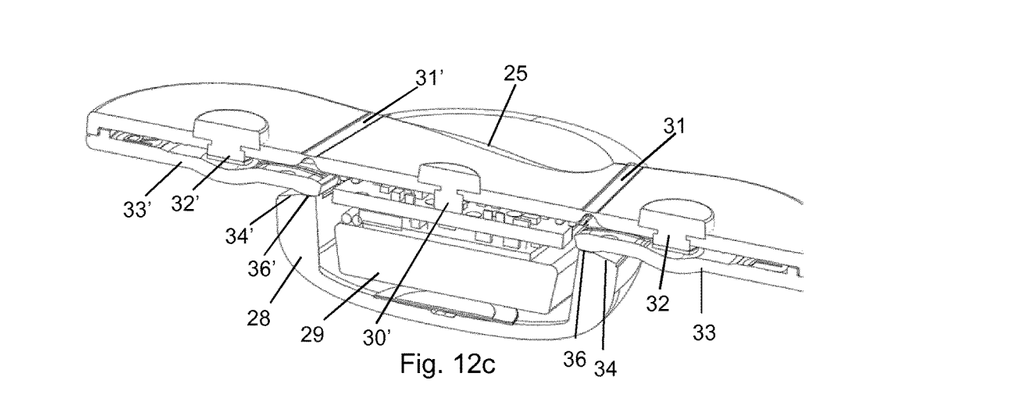
FIG. 12c shows a cut-through perspective illustration of the medical device of FIG. 2 showing the electrode housings.
Figure 12D:
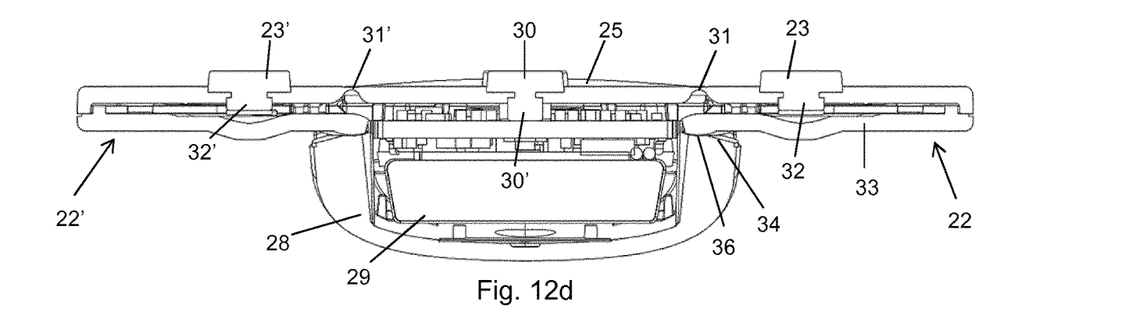
FIG. 12d shows a cut-through view from the back of the medical device of FIG. 2.

The presently disclosed medical device is preferably configured such that "in rest" the electrode are substantially arranged in the electrode plane, but when submitted to a pressure/force the wings can flex elastically from this plane. However, the medical device is preferably configured such that each of the two wings has a predefined maximal angular deflection from the electrode plane. The predefined maximal angular deflection may be more than ±5°, more preferably more than ±10°. The predefined maximal angular deflection may further preferably be less than ±30°, even more preferably less than ±20° and most preferably ±15°. As illustrated in FIGS. 12b, 12c and 12d the wings 22, 22' can rotate around an axis defined by the innermost side 38 of the wall the housing 28 having a camming surface 34. For the right wing 22 the predefined maximal angular deflection of the wing 22 can upwardly be defined by the interface 35 abutting the inside wall 38 of the housing 28. The distance from the interface 35 to the inside wall 38 determines the amount by which the wing 22 can be bent upwards. Bending downwards is limited by the camming surface 34, i.e. the angular gap formed between the camming surface 34 and the underside 33 of wing 22 defines the maximum angle of downward bending of the wing 22.

As discussed above in relation to the asymmetric substrate it is very important that any un-skilled user can take advantage of the presently disclosed medical device and use it correctly. Correct use might imply that the user must apply a disposable adhesive substrate on the electrodes in order to provide adhesive and conductive contact with the skin of user. If a one-to-one correspondence is provided between a substrate and a medical device it can be ensured that the substrate is applied correctly each time. One way of providing this correspondence is to provide some kind of pattern or trace on the medical device wherein the substrate fits in a unique way. This may be provided by one or more protrusions on the housing of the medical device extending from the electrode plane as exemplary illustrated in the drawings, most noticeable in FIG. 11 where the perspective field of view in the figure enhances the two protrusions 25, 25' provided on the electrode side of the medical device 21. The outline of the protrusion may be made asymmetric in order to match a corresponding asymmetric substrate. The maximal height of the protrusions is preferably less than the thickness of the corresponding substrate. E.g. the maximal height of the protrusions may be less than 1 mm.

As exemplified in the drawings the outline of the protrusion(s) in the electrode plane can be shaped as an asymmetric wave. The protrusion(s) may furthermore be rounded, preferably both the contour and the outline of the protrusion (s) are rounded, to avoid sharp edges that may be uncomfortable for the user. As also exemplified in the drawings (at least) two of said protrusions may be arranged to form a slot on the surface of the device. The protrusions are preferably arranged asymmetrically.

Hence, the presently disclosed medical device is preferably configured to receive a disposable adhesive substrate in the electrode plane on the surface of the housing, wherein the substrate is configured to form an adhesive bond between the medical device and the skin of the individual and configured to form a conductive connection between the electrodes and the skin of the user. Further, the medical device may be configured to receive a disposable adhesive substrate in a one-to-one correspondence on the surface of the housing in the electrode plane. E.g. the medical device may be configured to receive a disposable adhesive substrate in the abovementioned slot.

Figure 9:
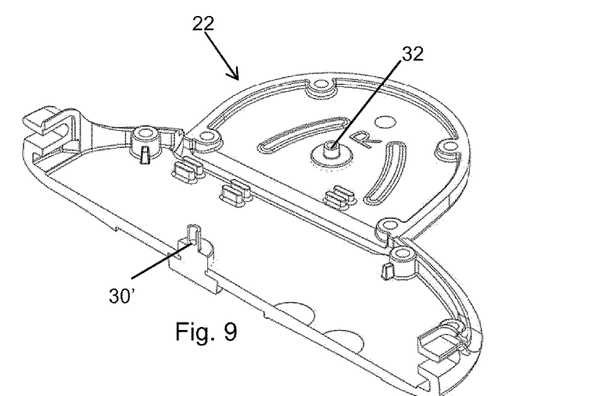
FIG. 9 shows a cut-through perspective illustration of a part of the housing of the medical device of FIG. 2 wherein the electrode housings are visible.

In a preferred embodiment of the presently disclosed medical device, the housing and the wings are at least partly manufactured in mouldable plastic and wherein the electrodes and terminals connecting the electrodes to the control unit are cast into and/or embedded into moulded plastic in the housing and the wings. An example of this is illustrated in FIGS. 9, 12c and 12d where the electrode terminals 30', 32 and 32' are embedded into the housing and the wings.

One way of avoiding wires is to provide wireless charging. Hence, in a preferred embodiment the presently disclosed medical device is configured such that the electrical power source can be wirelessly charged. The medical device is preferably also configured for storing data corresponding to measured and/or processed signals from muscular activity and configured for exchanging data with a terminal, e.g. the herein disclosed charging station.

The data exchange is preferably wireless, e.g. by means of infrared communication between medical device and terminal/charging station. In a further embodiment the medical device comprises two hollow pipes embedded in the housing and an infrared transmitter and an infrared receiver mounted in the housing, each of said IR units located in the housing at the end of one of said hollow pipes extending from the IR units to the shell of the housing, whereby said two-way infrared communication is provided via said hollow pipes. The hollow pipes thereby function as a sort of waveguide for the IR light. This is exemplified and illustrated in FIG. 10 and described in further detail below.

In the preferred embodiment the presently disclosed medical device is configured for receiving and monitoring electrical signals via said electrodes and/or providing electrical stimulation to said individual via said electrodes. Preferably the medical device is configured for receiving and monitoring electrical signals via said electrodes, and wherein the processing unit is configured for processing the received signals in order to detect said bruxism, and wherein the medical device is configured to generate a feedback signal in response to said detection of bruxism, the feedback in the form of electrical stimulation provided via said electrodes to a user of the device.

Detection of bruxism can be provided automatically as disclosed in pending application PCT/EP2015/060091 filed 7 May 2015 and entitled "Automatic detection of teeth clenching and/or teeth grinding". This application is hereby incorporated by reference in its entirety.

Charging Station

As previously stated another aspect of the present disclosure relates to a charging station for a wireless battery driven medical device comprising a housing with an upper cover, the upper cover having a recess shaped to hold the medical device in a one-to-one correspondence. An exemplary charging station is illustrated in the drawings, in particular FIGS. 5, 7, 10, 13 and 14.

As also exemplified in the drawings the contour of the recess may be at least partly rounded such that the recess is configured to match a rounded medical device, e.g. the medical device as herein disclosed. E.g. the contour of the recess is at least partly rounded such that a rounded medical device can slide into the recess. E.g. the contour of the recess is at least partly bowl shaped, and/or at least partly ellipsoid as exemplified in FIG. 13.

In a preferred embodiment the presently disclosed charging station is configured such that when the medical device is located in the recess the medical device can be slit out of the recess by pushing down on a predefined first area of the surface of the medical device. Hence, the charging station may be configured such that the medical device is securely located in the charger (like a bumblebee in a nest) but also such that the medical device can be picked up easily by pushing on a predefined part of the device. This is exemplified by the big black arrow in FIG. 7*d*. In addition the charging station may be configured such that when the medical device is located in the recess the medical device is fixed in the recess when pushing down on a predefined second area of the surface of the medical device, as exemplified by the big black arrow in FIG. 7*b*. This feature may be utilized during attachment of a disposable adhesive substrate on the medical device. This fixing in the recess may be provided by means of a protrusion on the upper cover of the charging station, a protrusion which may be covering, extending and/or protruding over at least a part of the recess, preferably such that when the medical device is located in the recess the protrusion is covering at least a part of the medical device. Hence, the charging station may be configured such that when pushing down on the second area of the surface of the medical device, an opposite side of the surface of the medical device engages with the protrusion such that the medical device is fixed in the recess, as exemplified by the protrusion 46 in FIG. 7*b*.

As also exemplified in the drawings, the recess of the charging station may be configured such that when the medical device is located in the recess the upper side of the medical device is substantially level with the upper side of the cover.

A further advantage of a recess in the charging station for a corresponding medical device is that it provides the option of arranging an induction coil around the recess such that wireless charging of the medical device can be enable when the device is located in the recess. Hence, the housing of the charging station preferably also comprises an induction coil surrounding the recess and configured such that the medical device can be wirelessly charged when located in the recess.

The presently disclosed charging station may further be configured for exchanging data wirelessly with the medical device. With the recess in the housing it can be ensured that the medical device is always arranged appropriately and in the correct configuration each time. This can be utilized for using infrared communication for the mutual data exchange between medical device and charging station, because IR communication usually requires a correct line of sight between transmitter and receiver.

In further embodiment the presently disclosed charging station comprises an assembly of visual signalling units, such as LEDs, located in the housing and configured to indicate 1) the status of charging the battery of a medical device located in the recess, and/or 2) the status of data exchange with between charging station and a medical device located in the recess. The assembly of visual signalling units may be configured to be visible on and/or through the upper cover when indicating the charging status and/or the data exchange status. This is exemplified in FIG. 14 where LEDs 48 are located at a circuit board of the charging station. Hollow pipes 48' leads to the upper cover 49; the upper surface of upper cover 49 is however unbroken. But light from the LEDs 48 can however penetrate the upper cover such that the LEDs can function as visual signalling units.

The assembly of visual signalling units may furthermore be configured such that the signalling units are substantially invisible and/or inactive after a predefined period of time of activation of the signalling units and/or after a predefined period of time of inactivation of the charging station. If the medical device is used for monitoring and treatment of nocturnal bruxism the charging station may well be located in the bedroom. Hence, with an automatic lights-off functionality the charging station is not lighting up the bedroom during the night. The charging station may further comprise a touch sensitive area, such as a capacitive touch sensitive area, located on the upper cover and configured such that the assembly of visual signalling units indicates the charging status and/or the data exchange status for a predefined period of time when the touch sensitive area is activated. This provides the option of requesting e.g. charging status even if the signalling units have turned off.

In a further embodiment the housing of the presently disclosed charging station comprises a non-slip bottom surface, preferably configured to provide a slip-resistant contact with a supporting surface, i.e. in order to provide a solid and sturdy support for the medical device that does not move when the device is placed in the charging station. The housing may further comprise a weight plate, preferably configured to increase the stability of the charging station when located on a supporting surface.

The presently disclosed charging station may further be configured to exchange data with a computing device, such as a smartphone, personal computer, etc. The data exchange with a computing device may be wireless, such by means of Bluetooth communication.

EXAMPLES

Figure 2A:
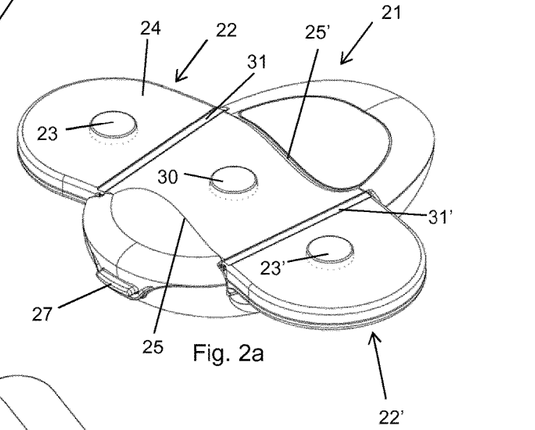
FIG. 2a shows a perspective bottom view of one embodiment of the presently disclosed medical device whereon the substrate of FIG. 1 can be applied.
Figure 2B:
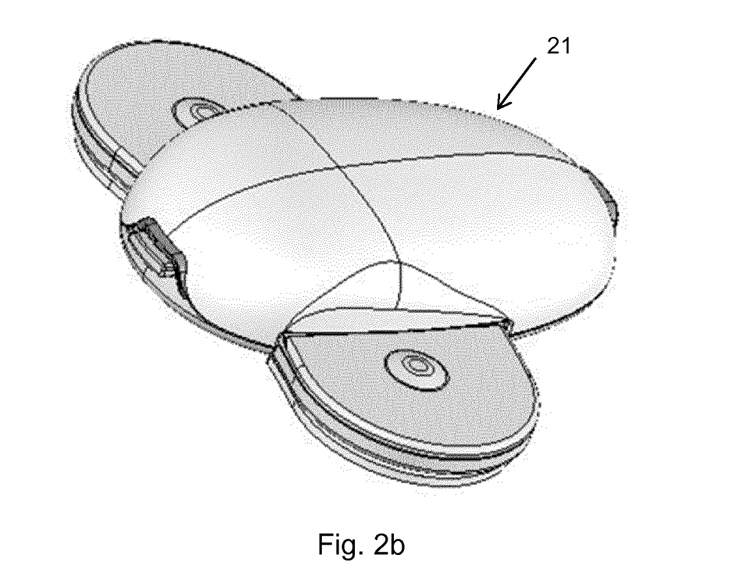
Figure 2C:
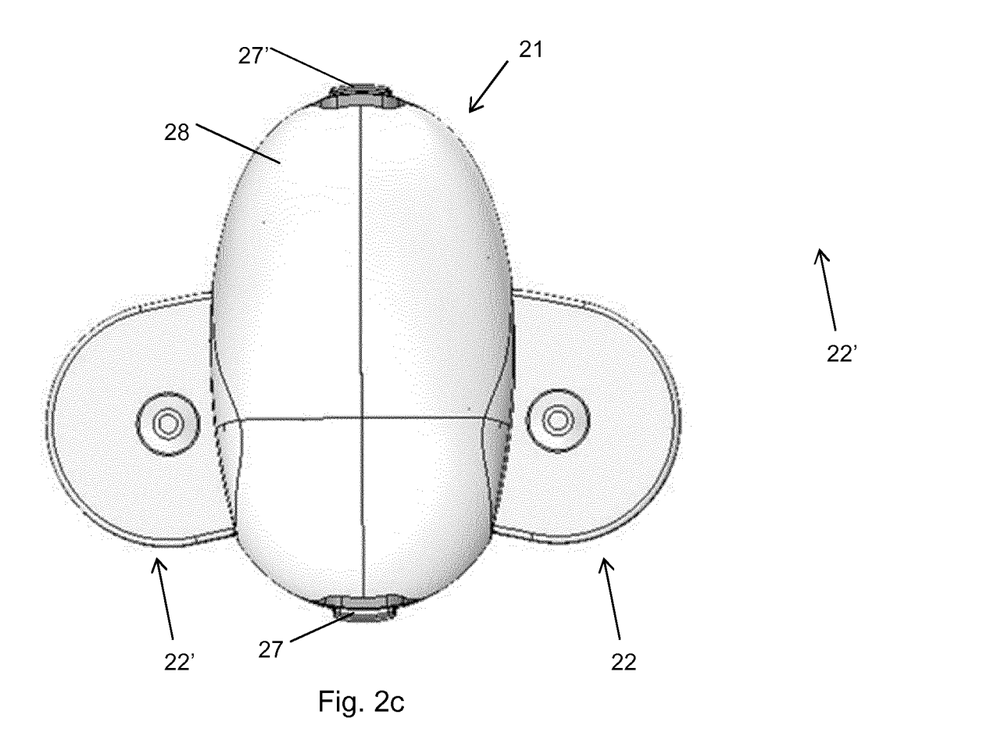

An example of the presently disclosed medical device 21 is illustrated in FIG. 2a showing a perspective bottom view of the device 21. It is the same exemplary medical device that is illustrated in all the drawings, in particular FIGS. 2b, 2c, 5, 7b, 7d, 8, 9, 10, 11, 12a-d and 14, and the numbering used is consistent in all figures. The medical device comprises two wings, right wing 22 and left wing 22' as illustrated in the top view in FIG. 2c that are hingedly connected to the housing 28. A centre EMG electrode 30 and an EMG electrode 23, 23' on each wing provides a total of three EMG electrodes that are protruding slightly from the electrode plane 24, whereon a disposable adhesive asymmetric substrate 1 can be applied.

Two push buttons 27, 27 are provided at opposite ends of the housing, the front button 27' and the back button 27. One of the push buttons is used to increase the stimulus level provided to the user upon detection of bruxism, the other push button is used to decrease this stimulus level. These are the only controls available to the user on the device itself and these are sufficient to control the device 21—many other features are automatic, e.g. auto start-stop, automatic adjustment of the background/noise level and automatic adjustment of the threshold level of bruxism for providing a stimulus signal. Additional controls and input settings can be provided and controlled via a computing device, such as a smartphone, which can be arranged to communicate with the device 21 via the charging station 41, e.g. by means of software, e.g. an App, running on the computing device.

The bottom side of the housing 28 of the medical device 21 protrudes slightly from the electrode plane 24 and two protrusions 25, 25' extends into the electrode plane 24 such that only a substrate with the outline as the substrate 1 in FIG. 1 can be applied to the electrode plane 24 in the slot/groove/trace defined between the protrusions 25, 25'.

FIGS. 12c-d show different cut-through front view illustrations of the medical device 21. The battery 29 is visible in the housing 28. The wings 22, 22' are hingedly attached to the housing 28. The upper electrode side of each wing 22, 22' is bendably attached to the upper side of the housing by means of a thinned connection formed by an elongated groove 31, 31' in the shell of the housing 28. The housing 28 has two camming surfaces 34, 34' to allow downwards bending of the wings 22, 22'. The interfaces 36, 36' of the undersides 33, 33' of wings 22, 22' constitute the points of contact during bending of the wings 22, 22'. The wings 22, 22' are bendable up and down, and if e.g. right wing 22 is bended upwards (with respect to the orientation of the medical device 21 in FIG. 12) the two surfaces 34, 36 will slide against each other but downwardly protruding edge 35 will eventually block the wing 22 from being bended further upward at a predefined bending angle of the wing 22. The distance from the edge 35 to the inside wall 38 determines the amount by which the wing 22 can be bent upwards.

Bending the wing 22 downwards is limited by the camming surface 34, i.e. the angular gap formed between the camming surface 34 and the underside 33 of wing 22 defines the maximum angle of downward bending of the wing 22, because when the wing 22 is bended downwards camming surface 34 will eventually abut the inner underside 33 of the wing 22 preventing the wing 22 from bending further downward. The same arrangement determining the maximum bending angles is provided for the left wing 22'. For the exemplary medical device 21 in FIG. 12 the wings 22, 22' are able to bend approx. 15° upwards and downwards, i.e. a maximum deflection of, in total, 30°.

Figures 7A, 7B:
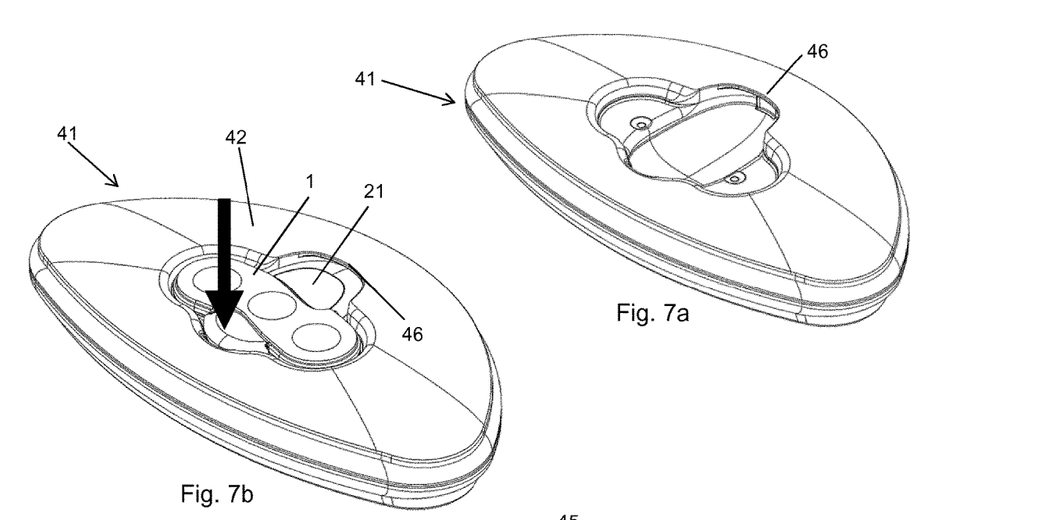
FIG. 7a shows a perspective illustration of one embodiment of the presently disclosed charging station having a recess for housing a medical device.
FIG. 7b shows a perspective illustration of the charging station of FIG. 7a where the medical device of FIG. 2 has been placed in the charger and where the substrate of FIG. 1 has been applied on the bottom of the medical device.

An example of the presently disclosed charging station 41 is illustrated in FIG. 7a showing a perspective top view of the device 41. It is the same exemplary charging station that is at least partly illustrated in FIGS. 5, 7a-d, 10, 13a-c and 14. This particular charging station 41 is configured to match (and charge) the illustrated medical device 21. The charging station 41 comprises a housing with an upper cover 42, the upper cover 42 having a recess 44 shaped to hold the medical device 21 in a one-to-one correspondence. As seen in the drawings the contour of the recess 44 is at least partly rounded such that the recess 44 is configured to match a medical device 21 with a rounded upper surface of the housing 28. In FIG. 7b the medical device 21 is located in the recess (nest) and a substrate 1 has been applied to the electrode surface of the device 21. The big black arrow indicated that if the device 21 is pushed downwards at the area the arrow is pointing, the protrusion 46 extending slightly over the recess 44 ensures that the device 21 is fixed in the recess 44. This is a good way to ensure that the device 21 is correctly arranged in the recess 44 and it is also a way to fix the device 21 in the recess when attaching the substrate 1 onto the device 21.

Figures 7C, 7D:
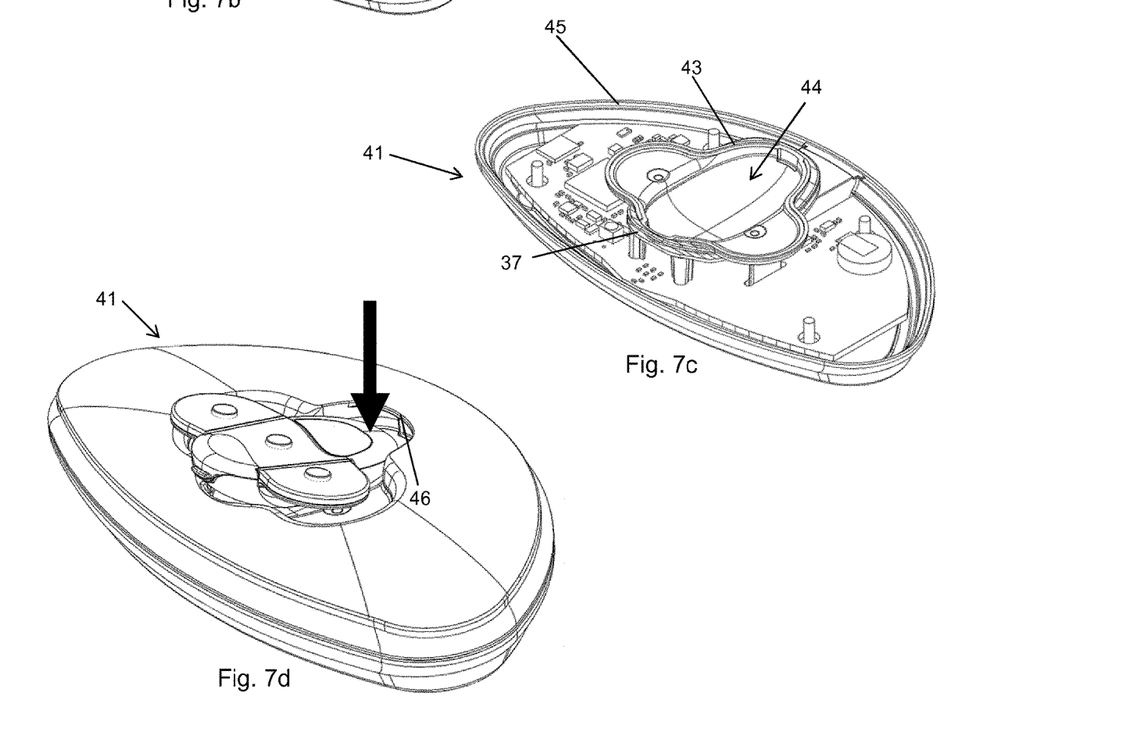
FIG. 7c shows a perspective illustration of the charging station of FIG. 7a where the upper cover has been removed.
FIG. 7d shows a perspective illustration of the charging station of FIG. 7a and the medical device of FIG. 2 during the process of removing the medical device from the charging station.
Figure 8:
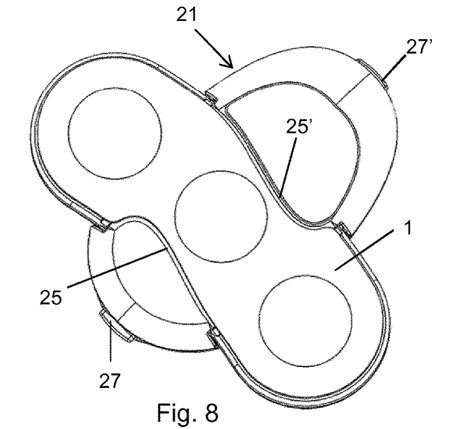
FIG. 8 shows the bottom of medical device of FIG. 2 whereon the substrate of FIG. 1 has been applied.

When pushing the opposite side of the device as illustrated in FIG. 7d, the rounded surfaces of the device 21 and the recess 44 provides for the device sliding out of the recess 44 as also indicated in FIG. 7d. The recess 44 in the housing provides for an elegant integration of the device 21 during charging but also for an easy removal of the device 21 by simply sliding it out of the recess 44.

Figure 13A:
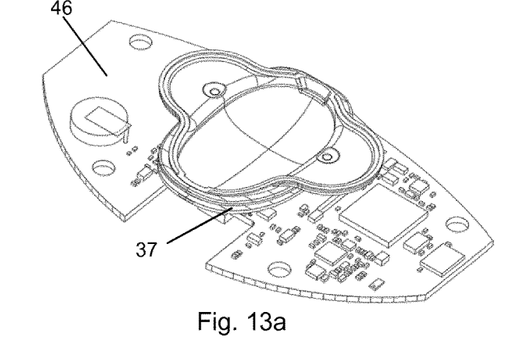
Figure 13B:
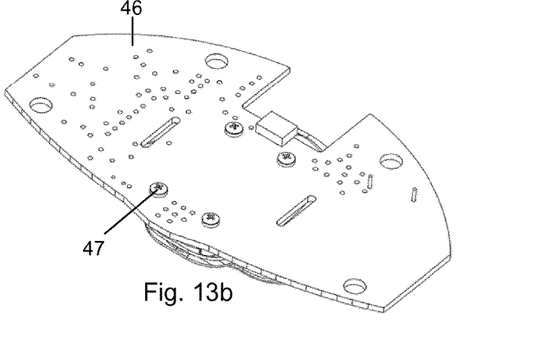
FIG. 13b corresponds to FIG. 13a showing the circuit board and the attachment of the recess.
Figure 13C:
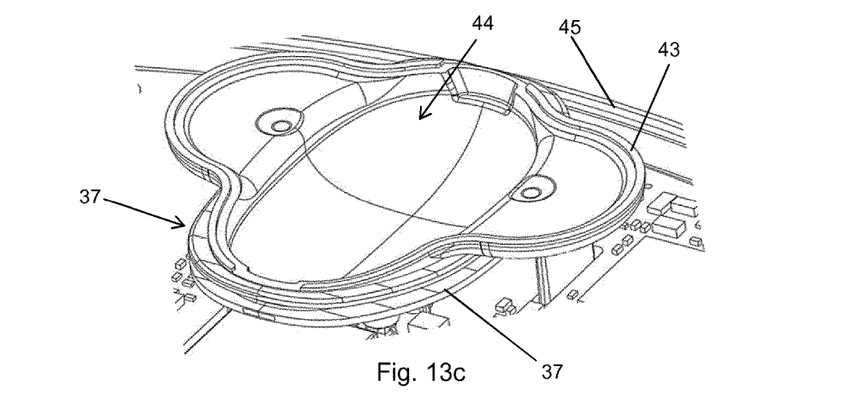
FIG. 13c is a perspective close-up view of the recess in FIG. 13a illustrating a trace for an induction coil for wireless charging.

FIG. 7c shows the charging station 41 without the upper cover 42. The lower cover 45 is now visible and visible is also the outline/edge 43 of the recess and the trace 37 for an induction coil such that wireless charging of the medical device 21 can be provided. The charging station 41 has been disassembled further in FIG. 13a-b showing the circuit board 46. It can be seen that the recess 44 is attached directly to the circuit board by means of screws 47. The trace 37 for the induction coil (not shown) is seen more clearly in FIG. 13c showing a close-up of the recess (nest) 44.

Figure 14:
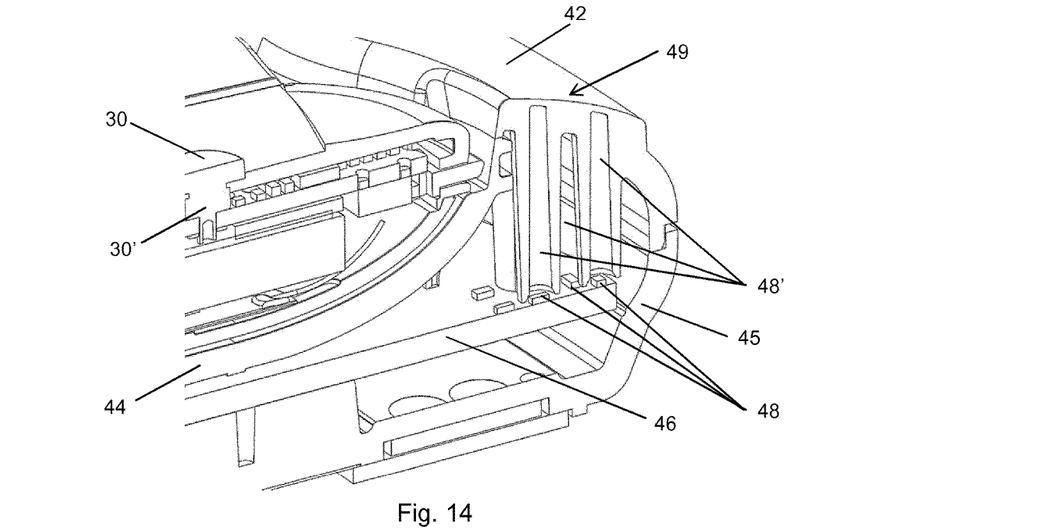
FIG. 14 shows a perspective cut-through illustration of the charging station of FIG. 7a with the medical device of FIG. 2 in the recess where light-tubes for indicating charging status are visible.

The cut-through illustration in FIG. 14 shows three hollow pipes 48' in the upper cover 42 such that three LEDs 48 on the circuit board 46 are visible through the upper cover 42, approx. at the position indicated by arrow 49.

Figure 10:
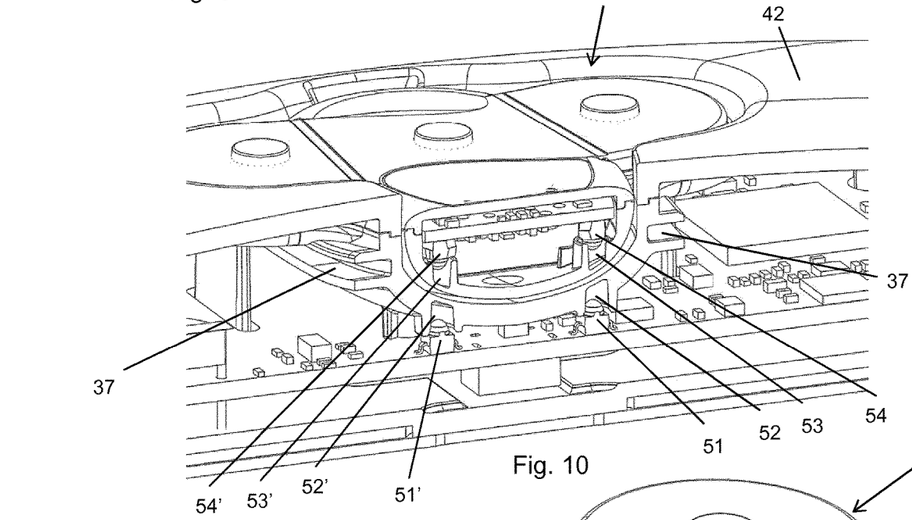
FIG. 10 shows a cut-through perspective illustration of the charging station of FIG. 7a with the medical device of FIG. 2 wherein the IR communication units are visible.
Figure 11:
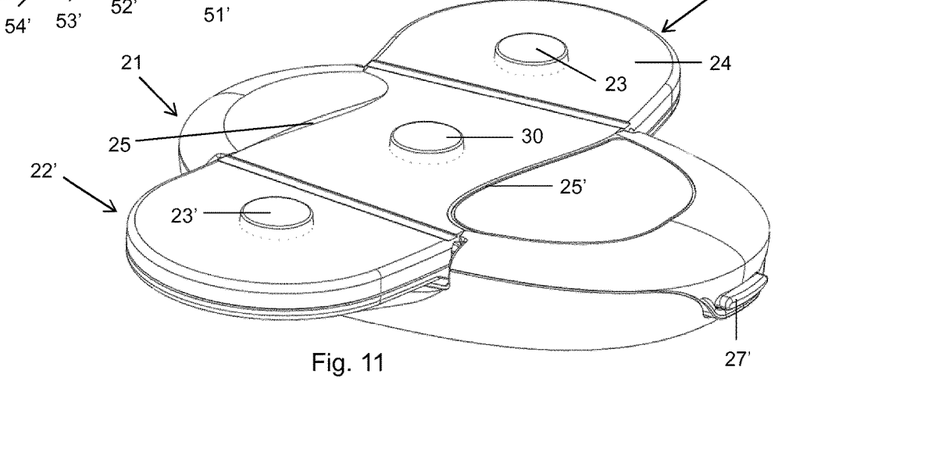
FIG. 11 shows a perspective illustration of the medical device of FIG. 2 wherein the protrusions of the medical device are visible.

Another cut-through illustration is shown in FIG. 10 where the device 21 is located in the charger 41. Two IR communication units 51, 51' are located in the charging station 41 and two IR communication units 54, 54' are located in the device 21 providing a total of four IR units. As seen in the drawings the IR units are paired and facing each other providing a line of sight between a transmitter in the charging station 41 and a receiver in the device 21, and between a receiver in the charging station 41 and a transmitter in the device 21. This line of sight vision is provided through hollow tubes/pipes 52, 52', 53, 53'.

Further Details—Items

The invention will now be described in further detail with reference to the following items:

1. A medical device for monitoring muscular activity of an individual comprising
   a housing for accommodating a power source, a control unit and a processing unit,
   two wings bendably attached to opposite sides of the housing, and
   at least three electrodes, such as EMG electrodes, mounted and distributed on the housing and each wing such that the electrodes extend substantially in a plane across the housing and the wings.
2. The medical device according to item 1, wherein the medical device is configured such that the wings can flexibly and/or elastically adapt to 1) the local contour of the skin of the individual, 2) to movement of the individual, and/or to muscular flexion and/or abduction of the individual.
3. The medical device according to any of the preceding items, wherein the medical device is configured such that the two wings are elastically bendable in the plane of the electrodes.
4. The medical device according to any of the preceding items, wherein the two wings are hingedly attached to the housing.
5. The medical device according to any of the preceding items, wherein the upper electrode side of each wing is bendably attached to the upper side of the housing by means of a thinned connection formed by an elongated groove in the shell of the housing, said elongated grooves forming the bending axes of the wings.
6. The medical device according to any of the preceding items, wherein the connection between the lower side of each wing (opposite the electrodes) and the housing is formed by means of an edge of the wing which is adapted to slide on a corresponding edge of the housing.
7. The medical device according to any of the preceding items, wherein the medical device is configured such that each of the two wings has a predefined maximal angular deflection from the electrode plane.
8. The medical device according to any of the preceding items 7, wherein the predefined maximal angular deflection of each wing is at least partly determined by camming surface defining a slope across the edge of the housing towards the underside of each wing.
9. The medical device according to any of the preceding items 7-8, wherein the predefined maximal angular deflection is at least partly determined by one or more protrusions formed on the inner edge of each wing, said protrusions adapted to engage the inner edge of the housing at a predefined angular deflection of the wings.
10. The medical device according to any of the preceding items 7-9, wherein the maximal angular deflection is more than ±10°, more preferably more than ±10°, and/or less than ±30°, even more preferably less than ±20° and most preferably approx.±15°.
11. The medical device according to any of the preceding items, further comprising one or more protrusions on the housing extending from the electrode plane.
12. The medical device according to any of the preceding items 11, wherein the outline of said protrusion(s) in the electrode plane is/are shaped as an asymmetric wave.
13. The medical device according to any of the preceding items 11-12, wherein said protrusion(s) is/are rounded.
14. The medical device according to any of the preceding items 11-13, comprising at least two of said protrusions arranged to form a slot on the surface of the device.
15. The medical device according to any of the preceding items 11-14, comprising at least two of said protrusions arranged asymmetrically to form a slot on the surface of the device.
16. The medical device according to any of the preceding items, configured to receive a disposable adhesive substrate in the electrode plane on the surface of the housing, said substrate configured to form an adhesive bond between the medical device and the skin of the individual and configured to form a conductive connection between the electrodes and the skin of the user.
17. The medical device according to any of the preceding items 11-16, configured to receive a disposable adhesive substrate in one-to-one correspondence on the surface of the housing in the electrode plane.
18. The medical device according to any of the preceding items 14-17, configured to receive a disposable adhesive substrate in said slot.
19. The medical device according to any of the preceding items 17-18, wherein the disposable adhesive substrate is the substrate according to any of items 1-77.
20. The medical device according to any of the preceding items, wherein the housing and the wings are at least partly manufactured in mouldable plastic and wherein the electrodes and terminals connecting the electrodes to the control unit are cast into and/or embedded into moulded plastic in the housing and the wings.
21. The medical device according to any of the preceding items, configured such that the electrical power source can be wirelessly charged.
22. The medical device according to any of the preceding items, configured for storing data corresponding to measured and/or processed signals from muscular activity and configured for exchanging data with a terminal.
23. The medical device according to any of the preceding items 22, wherein said data exchange is wireless.
24. The medical device according to any of the preceding items 22-23, wherein said data exchange is provided by means of infrared communication.
25. The medical device according to any of the preceding items 22-24, further comprising two hollow pipes embedded in the housing and an infrared transmitter and an infrared receiver mounted in the housing, each of said IR units located in the housing at the end of one of said hollow pipes extending from the IR units to the shell of the housing, whereby said two-way infrared communication is provided via said hollow pipes.
26. The medical device according to any of the preceding items 22-25, further comprising two hollow pipes embedded in the housing and an infrared transmitter and an infrared receiver mounted in the housing, each of said IR units located in the housing at the end of one of said hollow pipes extending from the IR units to the shell of the housing, whereby said two-way infrared communication is provided via said hollow pipes.
27. The medical device according to any of the preceding items, wherein the medical device is configured for receiving and monitoring electrical signals via said electrodes and/or providing electrical stimulation to said individual via said electrodes.

28. The medical device according to any of the preceding items, wherein the medical device is configured for receiving and monitoring electrical signals via said electrodes, and wherein the processing unit is configured for processing the received signals in order to detect said bruxism, and wherein the medical device is configured to generate a feedback signal in response to said detection of bruxism, the feedback in the form of electrical stimulation provided via said electrodes.

29. A charging station for a wireless battery driven medical device comprising a housing with an upper cover, the upper cover having a recess shaped to hold the medical device in a one-to-one correspondence.

30. The charging station according to any or preceding items 29, wherein the contour of the recess is at least partly rounded such that the recess is configured to match a rounded medical device.

31. The charging station according to any or preceding items 29-30, wherein the contour of the recess is at least partly rounded such that a rounded medical device can slide into the recess.

32. The charging station according to any or preceding items 29-31, wherein the contour of the recess is at least partly bowl shaped, and/or at least partly ellipsoid.

33. The charging station according to any or preceding items 29-32, configured such that when the medical device is located in the recess the medical device can be slit out of the recess by pushing down on a predefined first area of the surface of the medical device.

34. The charging station according to any or preceding items 29-33, configured such that when the medical device is located in the recess the medical device is fixed in the recess when pushing down on a predefined second area of the surface of the medical device.

35. The charging station according to any or preceding items 29-34, wherein the upper cover comprises a protrusion covering, extending and/or protruding over at least a part of the recess, preferably such that when the medical device is located in the recess the protrusion is covering at least a part of the medical device.

36. The charging station according to any or preceding items 34-35, configured such that when pushing down on the second area of the surface of the medical device, an opposite side of the surface of the medical device engages with the protrusion such that the medical device is fixed in the recess.

37. The charging station according to any or preceding items 29-36, wherein the recess is configured such that when the medical device is located in the recess the upper side of the medical device is substantially level with the upper side of the cover.

38. The charging station according to any or preceding items 29-37, wherein the housing further comprises an induction coil surrounding the recess and configured such that the medical device can be wirelessly charged when located in the recess.

39. The charging station according to any or preceding items 29-38, further configured for exchanging data wirelessly with the medical device.

40. The charging station according to any of the preceding items 29-39, wherein said data exchange is provided by means of infrared communication.

41. The charging station according to any of the preceding items 29-40, further comprising an assembly of visual signalling units, such as LEDs, located in the housing and configured to indicate 1) the status of charging the battery of a medical device located in the recess, and/or 2) the status of data exchange with between charging station and a medical device located in the recess.

42. The charging station according to any of the preceding items 42, wherein the assembly of visual signalling units are configured to be visible on and/or through the upper cover when indicating the charging status and/or the data exchange status.

43. The charging station according to any of the preceding items 41-42, wherein the assembly of visual signalling units are configured such that the signalling units are substantially invisible and/or inactive after a predefined period of time of activation of the signalling units and/or after a predefined period of time of inactivation of the charging station.

44. The charging station according to any of the preceding items 41-43, further comprising a touch sensitive area, such as a capacitive touch sensitive area, located on the upper cover and configured such that the assembly of visual signalling units indicates the charging status and/or the data exchange status for a predefined period of time when the touch sensitive area is activated.

45. The charging station according to any of the preceding items 29-44, wherein the housing comprises a non-slip bottom surface (configured to provide a slip-resistant contact with a supporting surface).

46. The charging station according to any of the preceding items 29-45, wherein the housing comprises a weight plate configured to increase the stability of the charging station when located on a supporting surface.

47. The charging station according to any of the preceding items 29-46, configured to exchange data with a computing device, such as a smartphone, personal computer, etc.

48. The charging station according to any of the preceding items 47, wherein the data exchange with a computing device is wireless, such as by means of Bluetooth communication.

49. A kit of parts comprising the medical device according to any of preceding items 1-28 and the charging station according to any of preceding items 29-48, wherein the medical device and the charging station are configured such that the medical device matches the recess of the charging station.

50. A disposable adhesive substrate adapted to be arranged on a medical device having EMG electrodes, the substrate comprising
    a first adhesive layer on a first plane side of the substrate configured for attaching the substrate to the medical device,
    a second adhesive layer on a second opposite plane side of the substrate configured for attaching the substrate to the skin of a user of the medical device, and
    conductive contact areas configured for providing electrical connection between the EMG electrodes and the skin of a user of the medical device.

51. The substrate according to any of the preceding items, wherein the circumferential outline of the substrate is laterally irreversible in the plane of the substrate.

52. The substrate according to any of the preceding items, comprising at least three of said conductive contact areas wherein the circumferential outline is axially asymmetric along an axis perpendicular to a line connecting the centres of the outermost contact areas.

53. The substrate according to any of the preceding items, comprising at least three of said conductive contact areas arranged in fixed isosceles triangular relationship one to another, wherein the circumferential outline of the substrate is axially asymmetric along an axis through the centre of the middle contact area which is perpendicular to a line connecting the centres of the outermost contact areas.

54. The substrate according to any of the preceding items, wherein the circumferential outline of the substrate is asymmetric along an axis through the centre the substrate.

55. The substrate according to any of the preceding items, wherein the circumferential outline of the substrate is asymmetric along two axes, preferably perpendicular axes, through centre the substrate.

56. The substrate according to any of the preceding items, wherein the circumferential outline of the substrate is asymmetric around any rotation axis, such any rotation axis in the plane of the substrate 57. The substrate according to any of the preceding items, wherein the circumferential outline of the substrate is asymmetric around a rotation axis which is perpendicular to the plane of the substrate.

58. The substrate according to any of the preceding items, wherein the circumferential outline of the substrate is configured to match a slot/groove on the medical device, such that the substrate and the medical device has a one-to-one attachment correspondence.

59. The substrate according to any of the preceding items, further comprising two cut-outs in the circumferential outline of the substrate.

60. The substrate according to any of the preceding items, further comprising at least two cut-outs in the circumferential outline of the substrate, wherein each cut-out is shaped like an asymmetric wave pulse.

61. The substrate according to any of the preceding items 59 to 60, wherein each cut-out is rounded.

62. The substrate according to any of the preceding items 59 to 61, wherein the cut-outs are asymmetrically arranged along the circumferential outline of the substrate.

63. The substrate according to any of the preceding items 59 to 62, wherein the shape of the cut-outs are configured to match a slot/groove on the medical device, such that the substrate and the medical device has a one-to-one attachment correspondence 64. The substrate according to any of the preceding items, wherein the circumferential outline of the substrate is axially asymmetric along a long axis in the plane of the substrate and axially asymmetric along an axis perpendicular to the long axis in the plane of the substrate.

65. The substrate according to any of the preceding items, wherein the circumferential outline of the substrate is substantially S-shaped.

66. The substrate according to any of the preceding items, further comprising apertures.

67. The substrate according to any of the preceding items, further comprising at least three apertures arranged in a fixed spatial relationship one to another.

68. The substrate according to any of the preceding items, further comprising at least three apertures arranged in a fixed triangular relationship one to another.

69. The substrate according to any of the preceding items, further comprising at least three apertures arranged such that centres of said apertures are not on a line.

70. The substrate according to any of the preceding items, further comprising at least three apertures arranged such that centres of said apertures lie on a line which is an arc of a circle having a radius of from 60-200 mm.

71. The substrate according to any of the preceding items 66 to 70, wherein each of said contact areas at least partly encircles a corresponding aperture.

72. The substrate according to any of the preceding items 66 to 71, wherein the centres of the apertures are arranged in a triangular arrangement in which the longest side of the triangle so defined is not more than 40 mm.

73. The substrate according to any of the preceding items 66 to 72, wherein the location and size of said apertures are configured to match the location and size of the EMG electrodes of the medical device.

74. The substrate according to any of the preceding items, configured to form an adhesive bond between the medical device and the skin of the user.

75. The substrate according to any of the preceding items, configured to form a conductive connection between the EMG electrodes and the skin of the user.

76. The substrate according to any of the preceding items, wherein the substrate is flexible and/or bendable.

77. The substrate according to any of the preceding items, further comprising two layers of removable protective sheet located on each plane side of the substrate.

The invention claimed is:

1. A disposable adhesive structure adapted to be arranged on a medical device having EMG electrodes, the structure comprising:
a substrate,
a first adhesive layer on a first plane side of the substrate configured for attaching the substrate to the medical device,
a second adhesive layer on a second opposite plane side of the substrate configured for attaching the substrate to the skin of a user of the medical device, and
conductive contact areas on the substrate configured for providing electrical connection between the EMG electrodes and the skin of a user of the medical device,
wherein the circumferential outline of the substrate is rotationally asymmetric around any two perpendicular rotation axes through the centre of the substrate and in the plane of the substrate.

2. The structure according to claim 1, wherein the circumferential outline of the substrate is asymmetric around every perpendicular rotation axis in the plane of the substrate.

3. The structure according to claim 1, wherein the circumferential outline of the substrate furthermore is asymmetric around a rotation axis perpendicular to the plane of the substrate.

4. The structure according to claim 1, comprising at least three of said conductive contact areas wherein the circumferential outline is axially asymmetric along an axis perpendicular to a line connecting the centres of the outermost contact areas.

5. The structure according to claim 1, comprising at least three of said conductive contact areas arranged in fixed isosceles triangular relationship one to another, wherein the circumferential outline of the substrate is axially asymmetric along an axis through the centre of the middle contact area which is perpendicular to a line connecting the centres of the outermost contact areas.

6. The structure according to claim 1, wherein the circumferential outline of the substrate is configured to match a slot/groove on the medical device, such that the substrate and the medical device has a one-to-one attachment correspondence.

7. The structure according to claim 1, further comprising two rounded cut-outs in the circumferential outline of the substrate.

8. The structure according to claim 7, wherein the cut-outs are asymmetrically arranged along the circumferential outline of the substrate.

9. The structure according to claim 7, wherein the cut-outs in the outline are shaped like an asymmetric wave pulse.

10. The structure according to claim 7, wherein the shape of the cut-outs are configured to match a slot/groove on the medical device, such that the substrate and the medical device has a one-to-one attachment correspondence.

11. The structure according to claim 1, wherein the circumferential outline of the substrate is substantially S-shaped.

12. The structure according to claim 1, further comprising at least three apertures in the substrate arranged in a fixed triangular relationship one to another.

13. The structure according to claim 12, wherein each of said contact areas at least partly encircles a corresponding aperture.

14. The structure according to claim 12, wherein the location and size of said apertures are configured to match the location and size of the EMG electrodes of the medical device.

15. The structure according to claim 1, wherein the substrate is flexible and/or bendable.

* * * * *